(12) United States Patent
Case (10) Patent No.: US 10,473,559 B2
(45) Date of Patent: Nov. 12, 2019

(54) AUTOMATED SOIL SAMPLE COLLECTION MACHINE WITH SCRAPER FOR REMOVING SURFACE DEBRIS (71) Applicant: James A. Case, Delaware, OH (US)

(72) Inventor: James A. Case, Delaware, OH (US)

( * ) Notice: Subject to any disclaimer, the term of this patent is extended or adjusted under 35 U.S.C. 154(b) by 110 days.

(21) Appl. No.: 15/728,824

(22) Filed: Oct. 10, 2017

(65) Prior Publication Data

US 2019/0107467 A1  Apr. 11, 2019

(51) Int. Cl.
*G01N 1/08* (2006.01)
*E21B 49/02* (2006.01)
*E02D 1/04* (2006.01)
*G01N 1/02* (2006.01)
*A01B 79/00* (2006.01)
*G01N 33/24* (2006.01)
*E02D 1/02* (2006.01)

(52) U.S. Cl.
CPC ............. *G01N 1/08* (2013.01); *A01B 79/005* (2013.01); *E02D 1/025* (2013.01); *E02D 1/04* (2013.01); *E21B 49/02* (2013.01); *G01N 2001/028* (2013.01); *G01N 2033/245* (2013.01)

(58) Field of Classification Search
CPC ........ E21B 49/02; E21B 25/00; E21B 25/005; E21B 25/16; G01N 1/08; G01N 2033/245; E02D 1/025; E02D 1/04; A01B 79/005
USPC ............................. 73/864.44, 864.45; 125/20
See application file for complete search history.

(56) References Cited

U.S. PATENT DOCUMENTS

| | | |
|---|---|---|
| 3,978,733 A | 9/1976 | Avot |
| 4,316,393 A | 2/1982 | Philipenko |
| RE30,901 E | 4/1982 | Boxrud |
| 4,685,339 A | 8/1987 | Philipenko |
| 5,076,372 A | 12/1991 | Hellbusch |
| 5,186,263 A | 2/1993 | Kejr et al. |
| 5,394,949 A | 3/1995 | Wright et al. |
| 5,408,893 A | 4/1995 | McLeroy |
| 5,419,211 A | 5/1995 | Rodel et al. |
| 5,741,983 A | 4/1998 | Skotnikov et al. |
| H0001780 H | 2/1999 | Melega |
| 5,931,236 A | 8/1999 | Mahlum et al. |
| 6,016,713 A | 1/2000 | Hale |
| 6,260,633 B1 | 7/2001 | Machek et al. |
| 6,360,829 B1 | 3/2002 | Naber et al. |
| 7,216,555 B2 | 5/2007 | Drummond et al. |

(Continued)

*Primary Examiner* — Herbert K Roberts
(74) *Attorney, Agent, or Firm* — Frank H. Foster; Kremblas & Foster (57) ABSTRACT

A soil sample collection machine has a mobile support frame that is transportable across the soil surface of an agricultural field. A surface scraper assembly is mounted to the mobile support frame and includes a scraper and a driver that is adapted to lower the scraper onto the surface of the soil and move the scraper across the soil surface for removing surface debris before a sample collection probe is driven into the soil at the scraped location and removes a soil sample. A soil sampling probe assembly is also mounted to the mobile support frame and includes a sample collection probe and a driver that is adapted to move the sample collection probe along a downward path into the soil to collect a sample of soil at the place the surface was scraped, to retract the probe upward and then to eject the soil sample from the probe into a container on an endless conveyer of containers.

10 Claims, 9 Drawing Sheets

(56) References Cited

U.S. PATENT DOCUMENTS

| | | | |
|---|---|---|---|
| 7,255,016 B2 | 8/2007 | Burton | |
| 8,159,357 B1 | 4/2012 | Jarvinen | |
| 8,573,074 B1 | 11/2013 | Marker | |
| 8,613,234 B1 | 12/2013 | Harrell | |
| 8,955,401 B1 | 2/2015 | Burton | |
| 9,116,078 B1 * | 8/2015 | Scheiderer | G01N 1/04 |
| 9,582,002 B2 | 2/2017 | Cavender-Bares | |
| 9,743,574 B1 * | 8/2017 | Maxton | A01B 79/005 |
| 9,759,637 B1 * | 9/2017 | Hellbusch | G01N 1/08 |
| 2013/0319763 A1 | 12/2013 | McGraw | |
| 2014/0251032 A1 * | 9/2014 | Scheiderer | G01N 1/08 |
| | | | 73/864.43 |
| 2015/0107503 A1 * | 4/2015 | Masten | A01B 79/005 |
| | | | 111/193 |
| 2017/0112042 A1 * | 4/2017 | Yi | A01B 33/021 |
| 2018/0080914 A1 * | 3/2018 | Baucom | G01N 33/24 |
| 2018/0124992 A1 * | 5/2018 | Koch | A01B 79/02 |
| 2018/0128933 A1 * | 5/2018 | Koch | G01S 13/02 |
| 2019/0059209 A1 * | 2/2019 | Brune | A01C 7/203 |
| 2019/0075714 A1 * | 3/2019 | Koch | G01B 7/26 |

\* cited by examiner

AUTOMATED SOIL SAMPLE COLLECTION MACHINE WITH SCRAPER FOR REMOVING SURFACE DEBRIS

CROSS-REFERENCES TO RELATED APPLICATIONS (Not Applicable)

STATEMENT REGARDING FEDERALLY-SPONSORED RESEARCH AND DEVELOPMENT (Not Applicable)

THE NAMES OF THE PARTIES TO A JOINT RESEARCH AGREEMENT (Not Applicable)

REFERENCE TO AN APPENDIX (Not Applicable)

BACKGROUND OF THE INVENTION

This invention relates generally to soil sampling and more particularly relates to automated soil sample collection machines that are mounted on a mobile support frame, such as a trailer, and towed across an agricultural field to collect multiple soil samples from multiple locations in the field.

As agriculture has become increasingly technically sophisticated, the collection of accurate data has become increasingly important to farmers. One source of useful data is the composition of the nutrients and other materials in the soil. Soil composition data assists the farmer in determining the particular materials and their concentration that are appropriate to add to the soil.

Agricultural fields usually consist of a top soil layer that is a mixture of relatively fine particles covered by a layer of debris such as cover crops and the leaves and stalks that remained after the harvest from the previous season. Because the seeds that are to be planted in the upcoming season grow root systems that rely on the soil layer for healthy growth and not on the debris layer, soil samples are more accurately analyzed if the soil samples do not include constituents from the debris layer. However, soil samples are commonly taken by plunging a hollow soil sampling probe down into the soil to retrieve a cylindrical core sample. Consequently, such soil samples include any of the debris layer components that lie on top of the soil above the cylindrical core sample. As a result, those debris layer components become mixed into the soil sample and are then included in the analysis results. Since the debris layer components are not a useful part of the soil, their inclusion in the soil sample causes inaccuracies in the analysis data.

It is therefore an object and feature of the invention to improve the accuracy of soil sampling analysis by eliminating the surface debris from the soil samples by removing the surface debris before the soil sample is collected by a soil sampling probe.

BRIEF SUMMARY OF THE INVENTION

The invention is a soil sample collection machine constructed on a mobile support frame that is transportable across the soil surface of an agricultural field. A soil sampling probe assembly is mounted to the mobile support frame and includes a sample collection probe and a first driver that is adapted to move the sample collection probe along a downward path into the soil to collect a sample of soil at the end of the downward path, to retract the probe upward and to eject the soil sample from the probe. A surface scraper assembly is movably mounted to the mobile support frame and includes a scraper and a second driver that is adapted to lower a scraper onto the surface of the soil and move the scraper across an intersection of said downward path with the soil surface for removing surface debris before the sample collection probe is driven into the soil and removes a soil sample.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

The invention is a soil sample collection machine that has its component parts mounted to a mobile support frame that is transportable across the soil surface of an agricultural field. The preferred mobile support frame is a trailer such as the trailer illustrated in U.S. Pat. No. 8,613,234 but could be a self-powered vehicle. The trailer is towed across a field by a motor vehicle, such as a truck or tractor, and periodically stops while a sample collection probe takes a soil sample and deposits the sample in a container. Preferably the mobile support frame also has a 12 v power supply that supplies power to an electrical sensor, solenoids that operate valves of a hydraulic circuit that operates drivers and their actuators and a PLC (programmable logic controller) that controls the solenoids. A gasoline engine drives a pump to supply hydraulic fluid under pressure to power the hydraulic cylinders and may also include an alternator to maintain the 12 v power supply. The electrical power system and the hydraulic hoses used with the invention are not illustrated because their use and configuration are well known in the prior art.

Figure 1:
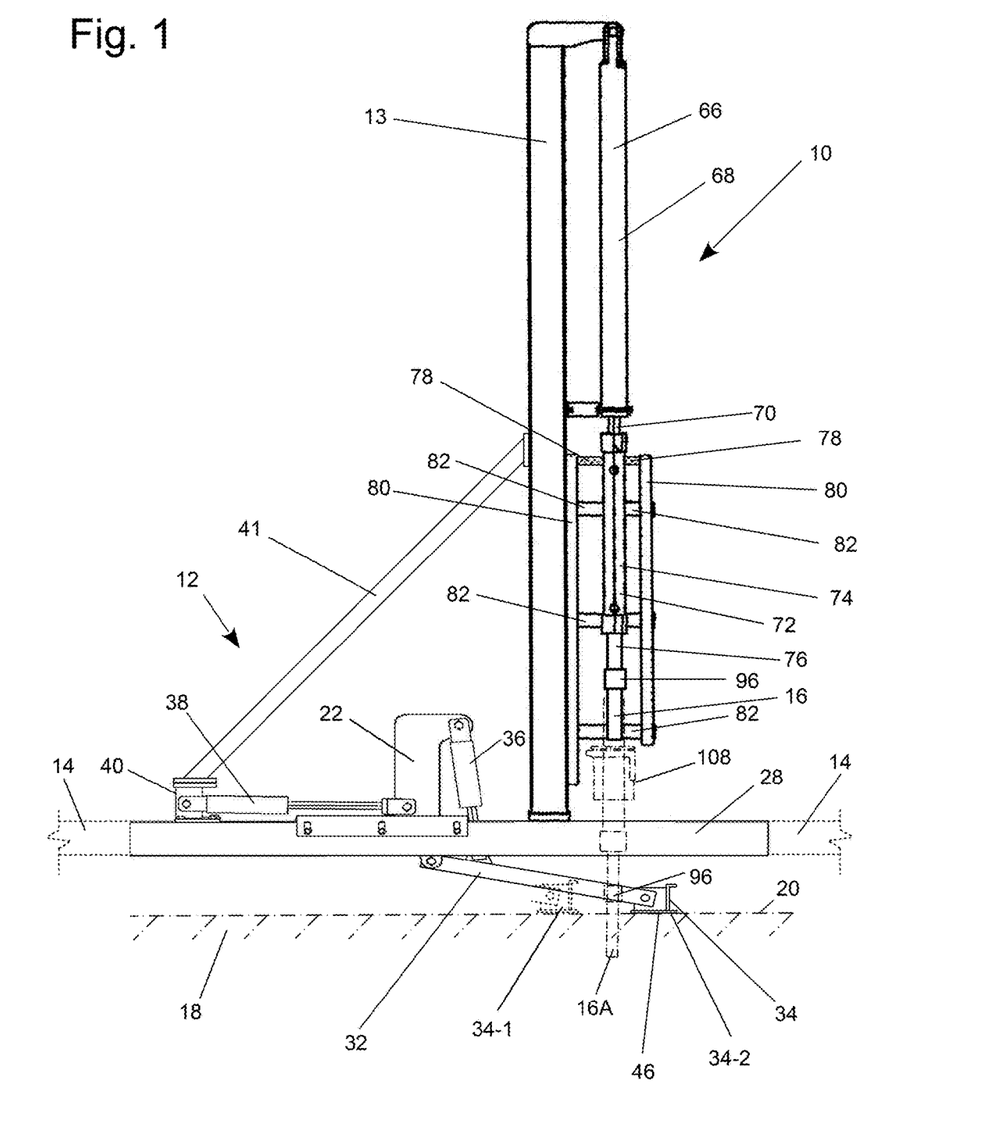
FIG. 1 is a view in side elevation of a soil sampling probe assembly and a surface scraper assembly mounted to a mobile support frame and embodying the invention.
Figure 2:
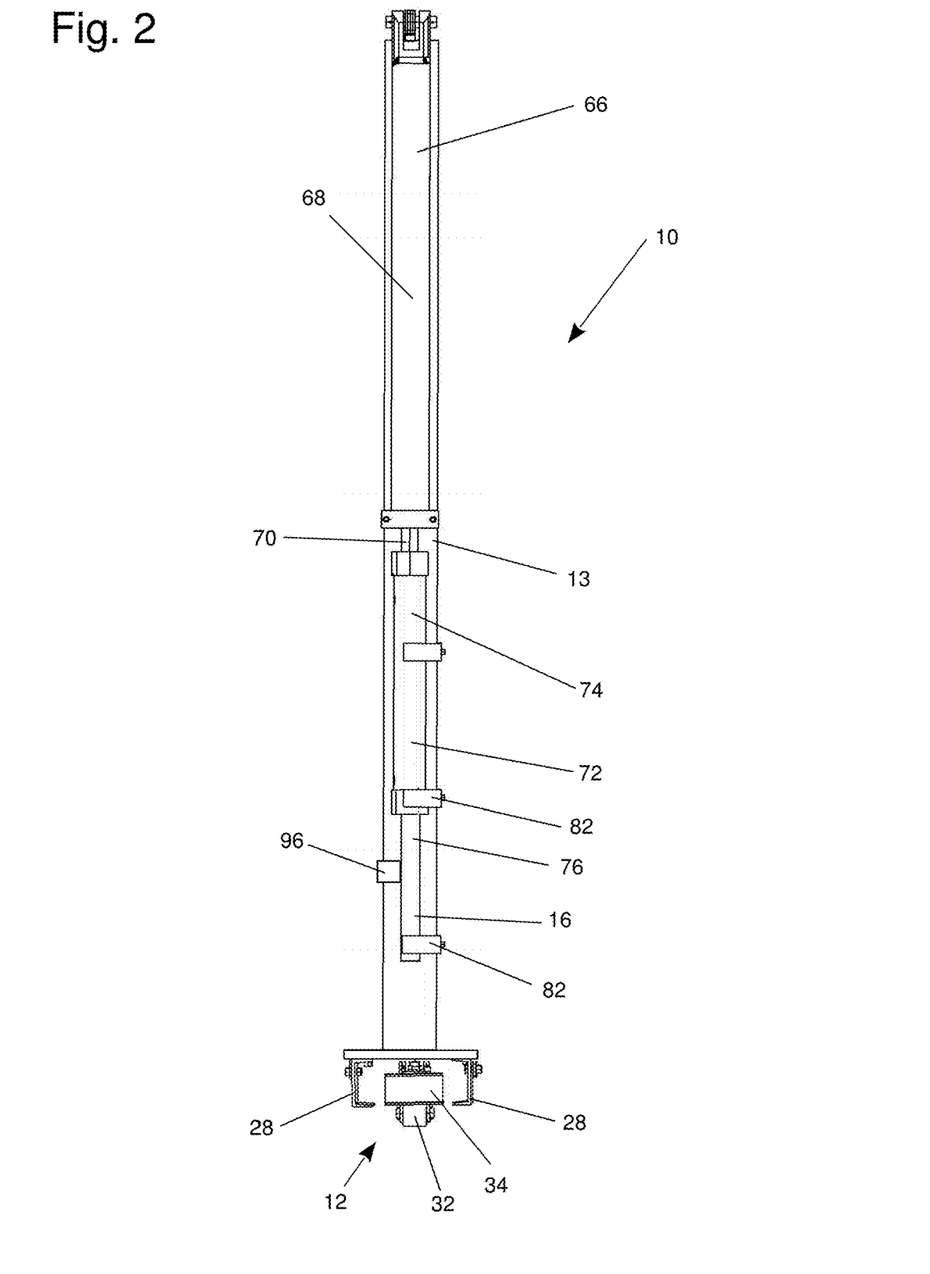
FIG. 2 is an end view in elevation of the embodiment illustrated in FIG. 1.
Figure 3:
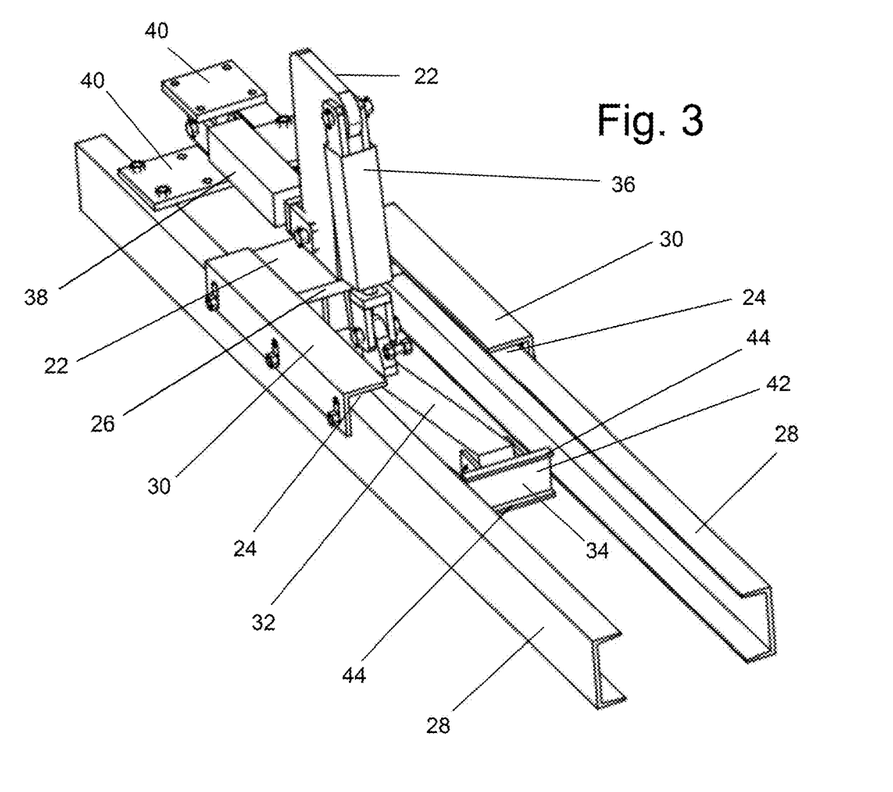
FIG. 3 is a view in perspective of the surface scraper assembly illustrated in FIGS. 1 and 2.
Figure 4:
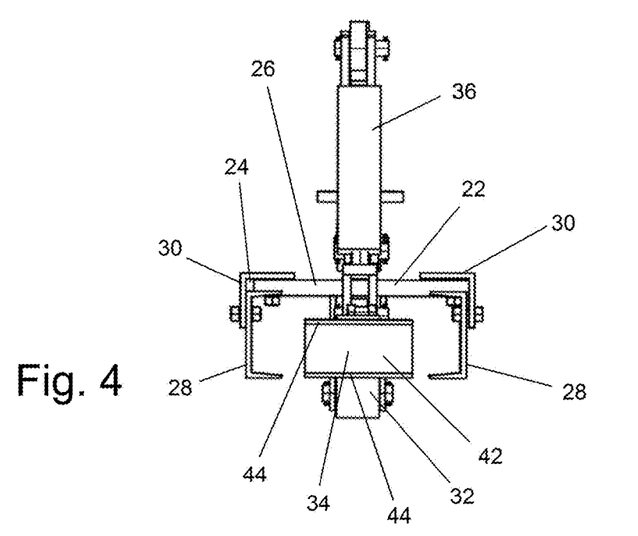
FIG. 4 is an end view of the surface scraper assembly illustrated in FIGS. 1 and 2.
Figure 5:
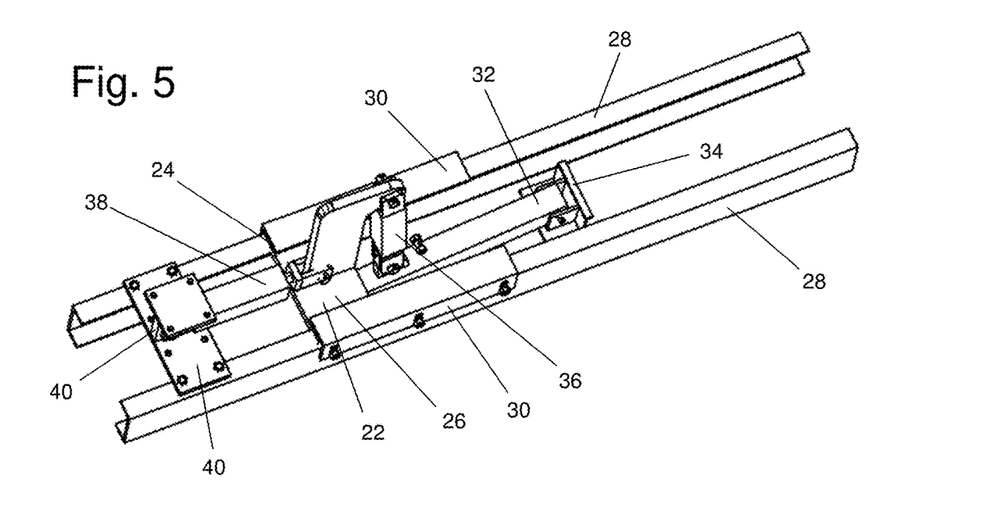
FIG. 5 is another view in perspective of the surface scraper assembly illustrated in FIGS. 1 and 2.
Figure 6:
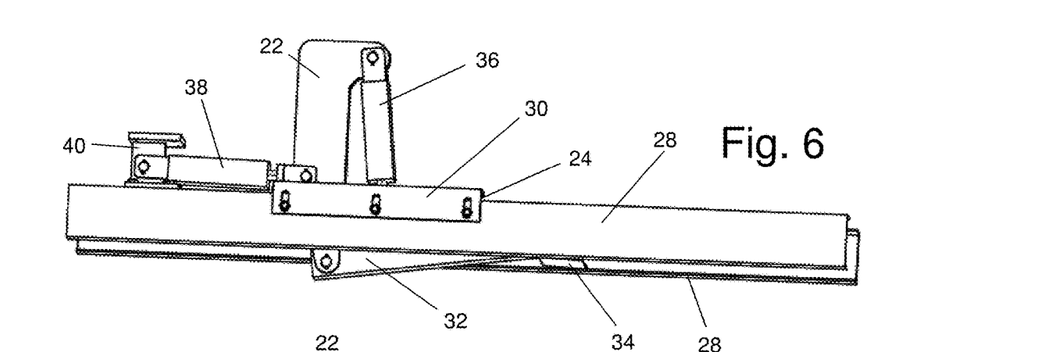
FIG. 6 is a side view of the surface scraper assembly illustrated in FIGS. 1 and 2.
Figure 7:
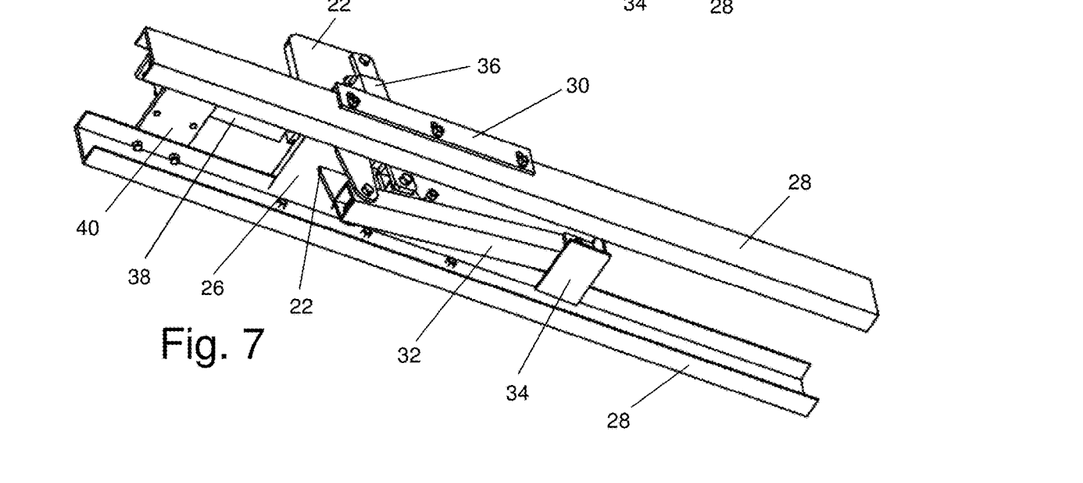
FIG. 7 is another view in perspective of the surface scraper assembly illustrated in FIGS. 1 and 2 and looking at its underside.

Referring to FIGS. 1 and 2, the two principal working component assemblies of the soil sample collection machine are a soil sampling probe assembly 10 and a surface scraper assembly 12, both of which are mounted to the mobile support frame. The soil sampling probe assembly 10 is mounted to a vertical support post 13 which is fixed to the mobile support frame 14. The soil sampling probe assembly 10 includes a sample collection probe 16 and a first driver (described below) that is adapted to move the sample collection probe 16 along a downward path into the soil 18 to collect a sample of soil at the end of the downward path and to retract the probe upward. The first driver also ejects the soil sample from the sample collection probe 16 and drops it into a container. The surface scraper assembly 12 includes a second driver (described below) that is adapted to lower its scraper onto the surface of the soil 18 and move the scraper across an intersection of the downward path of the sample collection probe 16 with the soil surface 20. This scraping of the soil surface 20 removes surface debris before the sample collection probe 16 is driven into the soil 18 and removes a soil sample.

The term "driver" is used to represent a mechanical prime mover or motor for moving one or more components of a machine. A driver may consist of one or more actuators with each actuator moving a subcomponent of a component. The preferred actuators are linear actuators in the form of hydraulic actuators (also known as hydraulic cylinders) which consist of a hollow cylindrical tube along which a piston slides. Actuators can be single acting when the fluid pressure is applied to just one side of the piston. In that case fluid pressure moves the piston in only one direction, a spring being frequently used to give the piston a return stroke. Actuators can also be double acting when fluid pressure is applied to one side or the other of the piston. Any difference in pressure between the two sides of the piston moves the piston in one direction or the other. The preferred embodiment is illustrated using double acting hydraulic actuators. An actuator ordinarily has two component parts that are forced apart or together to drive another component in one direction or the other. In common applications, one part is stationary and the other part moves. The stationary part may be called the stator and the moving part may be called the mover. Either part can be the stator with the other part acting as the mover. In most applications of a hydraulic actuator the cylinder is used as the stator and the piston with a piston rod attached to it operates as the mover.

Multiple different embodiments of the surface scraper assembly 12 are illustrated in FIGS. 1 through 12. FIGS. 1 through 7 illustrate one embodiment of the surface scraper assembly 12 and FIGS. 8 through 12 illustrate alternative embodiments. The embodiments differ with respect to the particular ground contacting scraper that is used because there are multiple different ground contacting scraper embodiments that can be interchangeably substituted for each other.

FIGS. 1 through 7 illustrate a surface scraper assembly 12 embodying the invention. A carriage 22 is slidable along a track 24 that is attached to the mobile support frame 14. More particularly the carriage 22 includes a plate 26 that slides along the track 24 that is formed by a gap between cross beams 28 and shorter L-beams 30. A scraper support arm 32 is pivotally mounted near a first end to the carriage 22 so it can rotate with respect to the carriage 22. A scraper 34 is mounted near an opposite second end of the support arm 32 for removing debris from the soil surface. The driver for the surface scraper assembly 12 is preferably formed by two hydraulic actuators. The first actuator 36 is attached between the carriage 22 and the scraper support arm 32. The first actuator 36 at times lowers the scraper 34 down onto the soil surface 20 and at times raises the scraper 34 from the soil surface 20. A second actuator 38 is attached at one end to the mobile support frame 14 via an upstanding support bracket 40 that is attached to the cross beams 28. The opposite end of the second actuator 38 is attached to the carriage 22. The second actuator 38 at times extends the scraper 34 by sliding the carriage 22 along the track 24 and thereby moving the scraper 34 horizontally along the soil surface 20 and across the downward path beneath the sample collection probe 16. The second actuator 38 at times retracts the carriage 22 and with it the scraper 34 by returning them to the positions illustrated in FIGS. 3 through 7. As illustrated on FIG. 1, a tubular stabilizer brace 41 is attached at its opposite ends between the support bracket 40 and the vertical support post 13.

There are multiple different scrapers that are interchangeably mountable to the scraper support arm 32. Each can be selected to best accommodate different soil conditions and different debris conditions on the soil surface 20.

One scraper embodiment 34 is shown in more detail in FIGS. 3 through 7. This scraper 34 is a push blade scraper which means it is similar to a bulldozer blade. Preferably it has vertical blade 42 carrying top and bottom flanges 44 and a bottom horizontal plate 46 for sliding along the soil surface 20. As illustrated in FIG. 1, the scraper 34 is operated by first moving it down onto the soil surface 20 to position 34-1 (illustrated in phantom) and then sliding the scraper 34 along the soil surface 20 to position 34-2. This motion pushes and clears debris from an area below the sample collection probe 16. The scraper 34 is then raised back up and retracted back to its original position. The sample collection probe 16 is then lowered through the cleared area into the soil 18 to position 16A (in phantom) to obtain a core sample and is then raised back into position. Preferably the scraper assembly 12 is oriented laterally of the direction of travel of the trailer so the scraper 34 scrapes the soil and pushes the debris laterally of the trailer's direction of travel to push debris sideward although that orientation is not essential.

Figure 8:
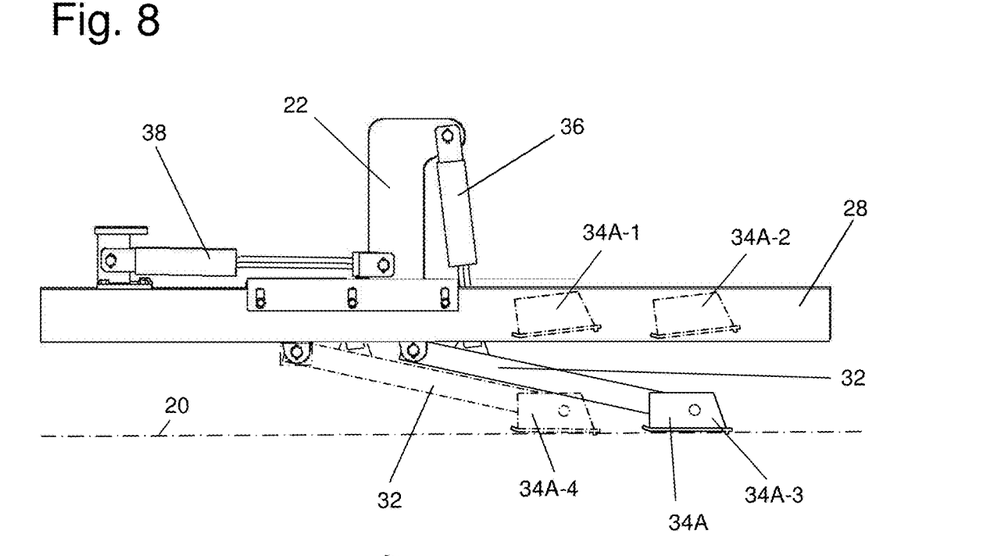
FIG. 8 is a side view of the surface scraper assembly illustrated in FIGS. 1 and 2 but showing a different embodiment of the scraper and the sequence of motions of the scraper.
Figure 8A:
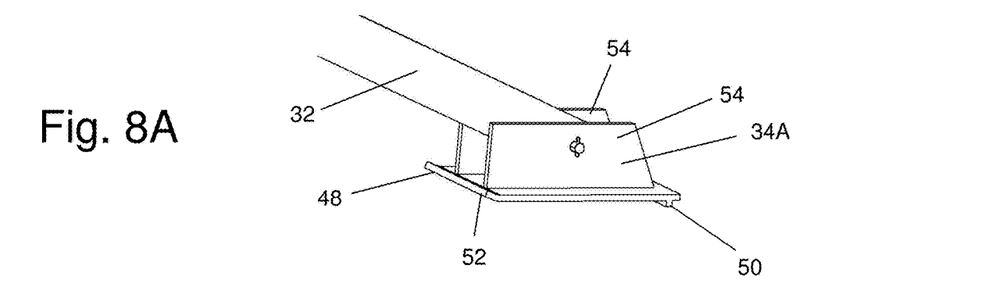
FIG. 8A is a view in perspective of the surface scraper illustrated in FIG. 8.
Figure 8B:
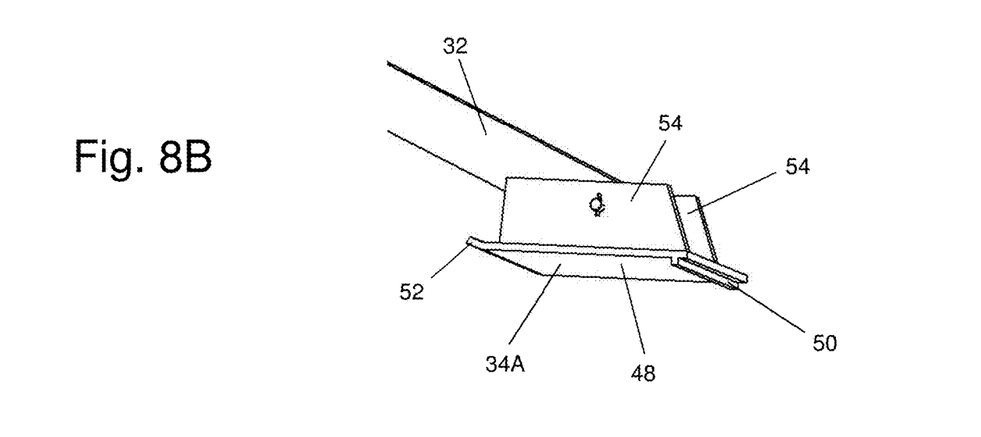
FIG. 8B is a view in perspective of the scraper embodiment illustrated in FIG. 8 and looking at it from a different perspective.
Figure 9:
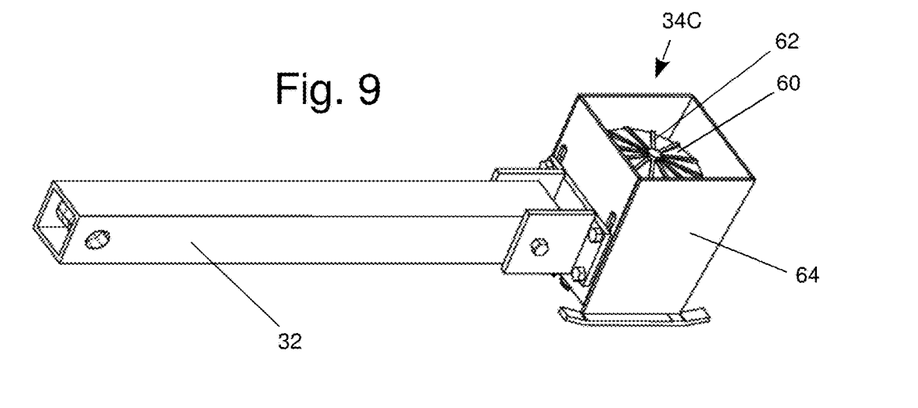
FIG. 9 is a view in perspective of yet another scraper embodiment seen from a downward perspective.
Figures 10, 11:
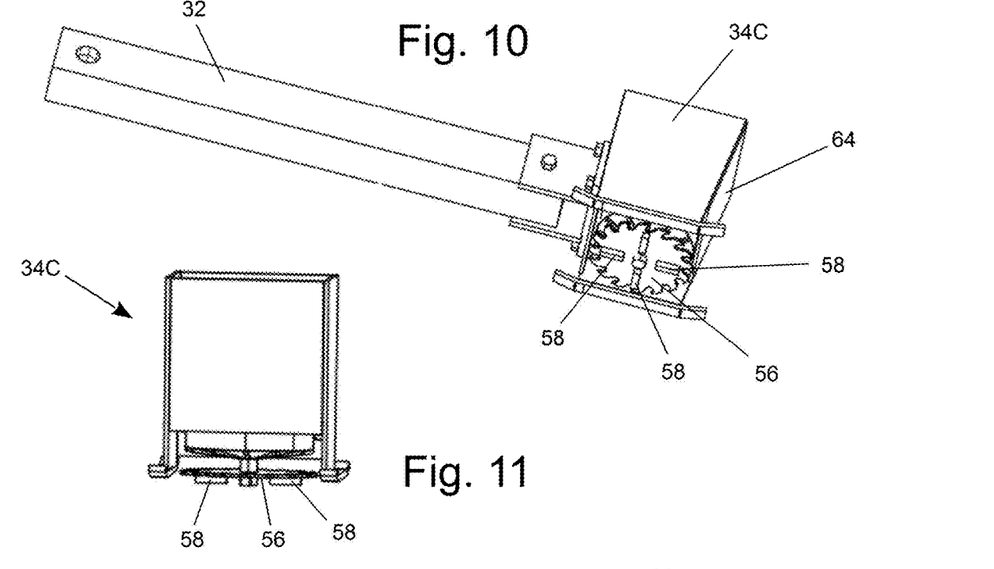
FIG. 10 is another view in perspective of the scraper embodiment of FIG. 9 seen from an upward perspective.
FIG. 11 is an end view of the scraper embodiment illustrated in FIG. 9.
Figure 12:
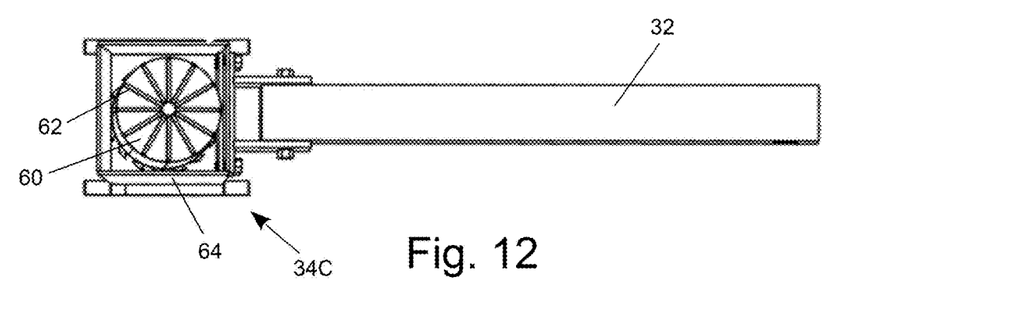
FIG. 12 is a top view of the scraper embodiment illustrated in FIG. 9.

FIGS. 8, 8A and 8B illustrate a scraper 34A that is preferred for the most common field conditions. The scraper 34A is a drag scraper that has a horizontal base plate 48 with a downward protruding ridge 50 on the underside of the base plate 48. The downward protruding ridge 50 is oriented transversely of the scraper support arm 32 and therefore transversely to the direction of travel of the scraper 34A across the soil surface 20. Preferably the downward protruding ridge 50 is positioned distally from the support arm so it is near the trailing edge of the scraper 34A as it travels across the soil surface 20. Desirably the scraper 34A has an upturned opposite leading end 52 formed in the base plate 48. A pair of upstanding ribs 54 are fixed to the base plate 48 for pivotal attachment of the scraper 34A to the scraper support arm 32.

The operation of the drag scraper 34A is illustrated in FIG. 8. When not in use the drag scraper 34A is carried in the position 34A-1. For clearing debris before a sample is taken, the drag scraper 34A is moved to the position 34A-2 and then lowered onto the soil surface 20 to position 34A-3. The drag scraper 34A is then slid across the soil surface 20 to the position 34A-4 to scrape debris away from the location where the soil sample will be taken and then raised back to position 34A-1. As with the motion of all of the scraper embodiments, the particular motions do not have to be made independently one at a time but rather can be made with both actuators 36 and 38 operating simultaneously to move the scraper with simultaneous combinations of two motions.

FIGS. 9 through 12 illustrate a third scraper embodiment which is a cutter scraper 34C. The cutter scraper 34C is designed for use when there is a thicker layer of cover debris on the soil surface and/or stubble protruding from the soil surface. The cutter scraper 34C has a cutter blade 56, which may be configured similarly to a circular saw blade, and is driven in rotation by an internally mounted electric motor (not visible) so it can cut through debris on the soil surface. A plurality of outward extending and preferably radially extending vanes 58 are fixed to the underside of the cutter blade 56 so they rotate rapidly with the cutter blade 56. The rotating vanes 58 operate to throw cut debris outward away from the cutter blade 56 in order to leave the soil surface bare at the position where the soil sample is to be extracted. The electric motor shaft that is connected to the center of the cutter blade 56 for driving it in rotation is also connected at its upper end to a motor cover disk 60 that is also driven in rotation by the electric motor. The motor cover disk 60 also has outward, preferably radially extending, vanes 62 that similarly serve to throw out any cut debris that is carried by air currents and floats down onto the top of the cutter scraper 34C. The cutter scraper 34C has a protective surrounding box 64 that functions somewhat like a mower deck and also pushes any highly piled debris away from the soil surface where the soil sample is to be taken. The cutter scraper 34C can be operated in the same manner as either the push blade scraper 34 or the drag scraper 34B, although operation in the manner of the former is preferred.

FIGS. 1, 2, 13 and 14 illustrate an embodiment of the soil sampling probe assembly 10. Its component parts are operated by a driver that comprises an upper hydraulic actuator 66 that has its stator 68 (preferably its cylinder) fixed to the mobile support frame via its attachment to the support post 13. The mover 70 of the upper hydraulic actuator 66 extends downward and is fixed to the upper end of the stator 72 (preferably the cylinder) of a lower hydraulic actuator 74. A sample receiving tube 76, which has an internal central passageway, is fixed to the lower end of the stator 68 of the upper hydraulic actuator 66 and forms the sample collection probe. The mover of the lower hydraulic actuator 74 extends downward and has a fixed connection to a rod that is slidable within and along the central passageway of the sample receiving tube 76. The mover of the lower hydraulic actuator 74, the central passageway and the central rod that is slidable within and along the central passageway are not visible because they are within the lower hydraulic actuator 74 and the sample receiving tube 76.

Figure 13:
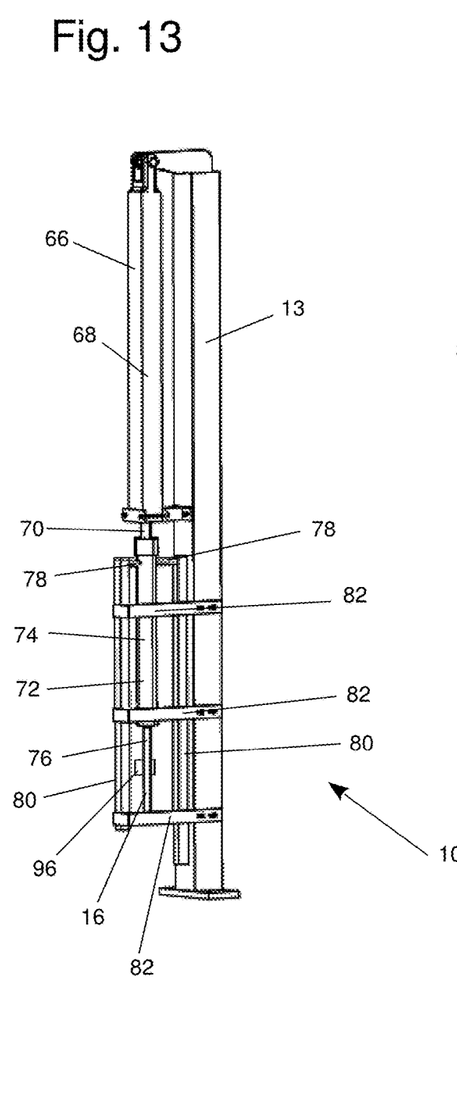
FIG. 13 is a side view of the soil sampling probe assembly illustrated in FIG. 1.
Figure 14:
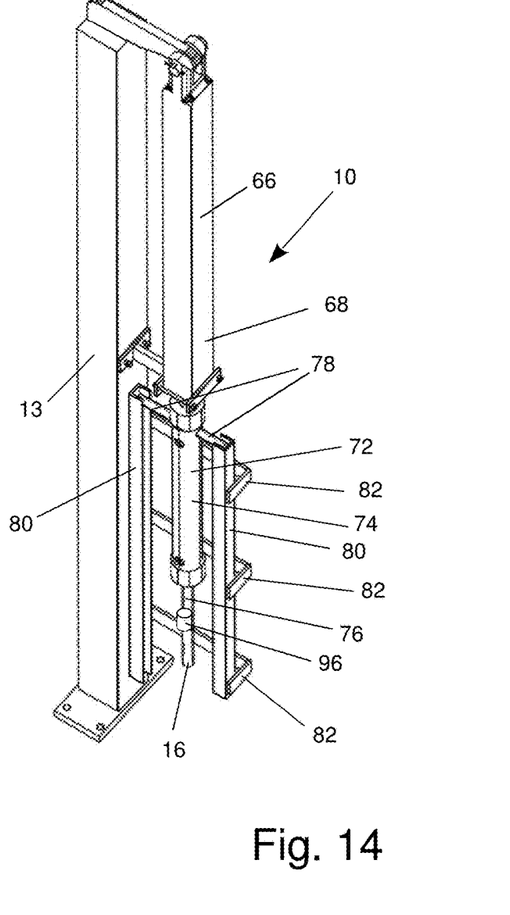
FIG. 14 is a view in perspective of the soil sampling probe assembly illustrated in FIG. 1.

In the operation of the soil sampling probe assembly 10 to extract a soil sample, the upper actuator 66 lowers the lower actuator 74 and with it lowers the sample receiving tube 76 through the soil surface into the soil 18 and collects a soil sample within the central passageway. The upper actuator 66 then raises the lower actuator 74 and with it the sample receiving tube 76. A sample container is then moved under the sample receiving tube 76. The lower actuator 74 is then operated to slide the central rod downward and along the central passageway to eject the soil sample from the sample receiving tube 76 and the soil sample falls into the container.

In order to guide the lower actuator 74 and the sample receiving tube 76 along a vertical path and prevent their rotation, a horizontal guide bar 78 extends through and is attached to the lower actuator 74. Its opposite ends form arms that extend radially outward. The guide bar 78 extends into a pair of vertical, U-shaped guide channels 80 (omitted from FIG. 2 in order to reveal the components behind them in FIG. 2). The outer ends of the guide bar 78 slide up and down within the U-shaped guide channels 80. The guide channels 80 are fixed to and supported by horizontal support arm 82 that are attached to the vertical support post 13.

Operation of embodiments of the invention can be enhanced by the addition of one or more of the following features: (1) detection of a rock or other hard barrier in or on top of the soil; (2) sensing and controlling the depth of penetration into the soil of the sample collection probe 16 (sample receiving tube 76); and (3) maintaining a downward force on the scraper as it moves across the soil surface 20 scraping away surface debris.

Figure 16:
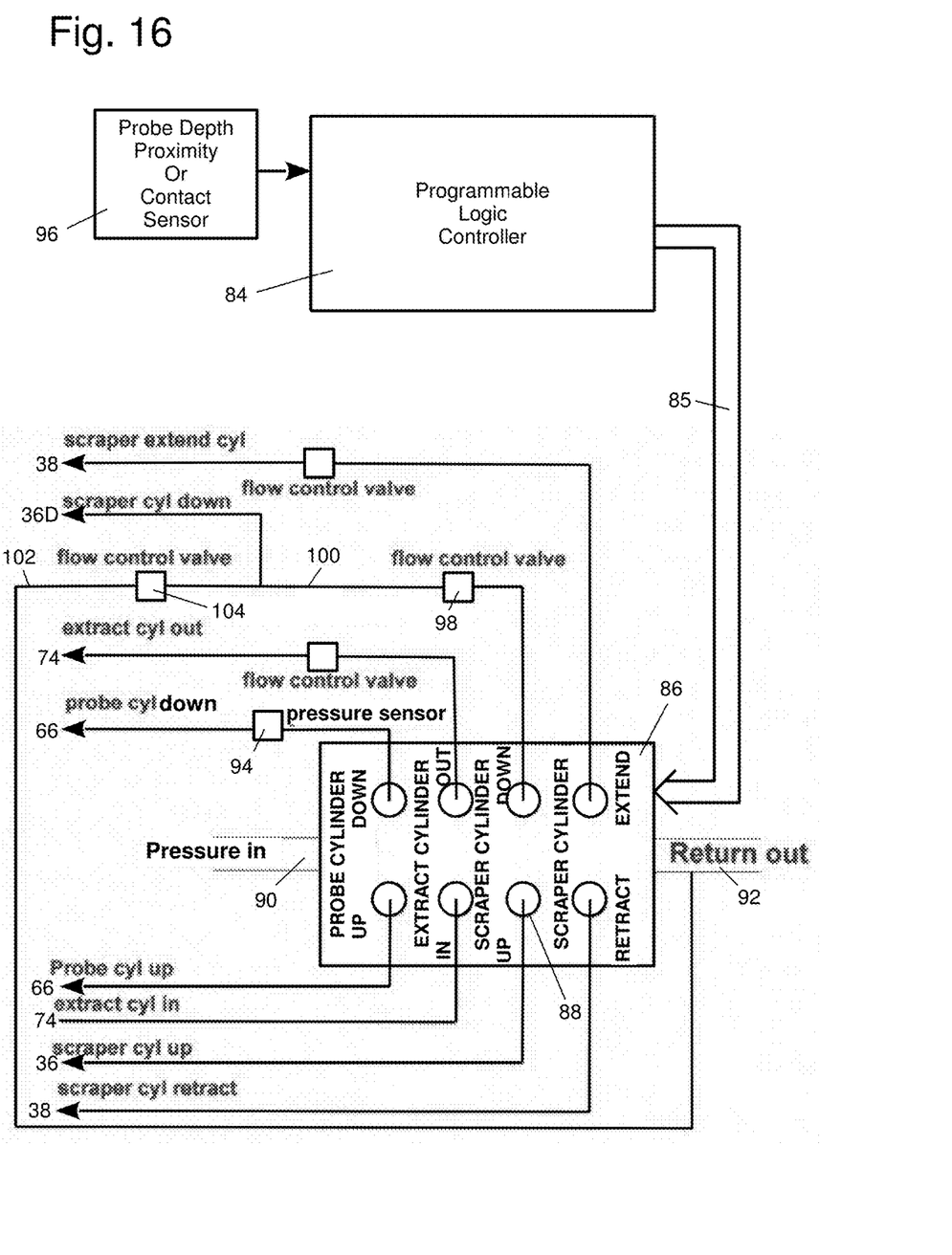
FIG. 16 is a hydraulic circuit schematic diagram of an embodiment of the invention.

In order to describe these three features, the hydraulic and electric circuit is illustrated in FIG. 16. The hydraulic actuators are controlled by software stored in the PLC 84 that is programmed to operate the actuators as described above. The PLC 84 is electrically connected through a multi-conductor cable 85 to a commercially available hydraulic manifold 86 that has eight hydraulic outlet ports 88 in hydraulic connection through conventional hydraulic fluid conducting hoses and/or rigid pipes to the hydraulic actuators. The manifold 86 also has the conventional pressure in port 90 and hydraulic fluid return port 92. The eight outlet ports 88 are controlled by four solenoid actuated valves that selectively apply hydraulic fluid pressure to one side or the other of the pistons of the double acting hydraulic actuators and simultaneously connect the opposite side of the pistons of the double acting hydraulic actuators to the return. The particular actuators to which the manifold outlet ports 88 are connected are shown by the reference number of the actuator at the arrow heads along the left side of FIG. 16. The side of the actuators to which the manifold outlet ports 88 are connected to the hydraulic pressure is indicated by the function terms in, out, up, down, retract and extend. As can be seen in FIG. 16, some of the manifold outlet ports 88 are connected to the actuators through additional hydraulic components.

The feature for detecting a rock or other hard barrier in or on top of the soil is provided by a barrier pressure sensor 94 in the hydraulic line that feeds the hydraulic cylinder 66 for lowering the sample collection probe 16 into the soil. The barrier pressure sensor 94 is electrically connected to the PLC 84 and senses a hard barrier. In particular, when the hydraulic pressure that is lowering the hydraulic cylinder 66 exceeds the set point pressure of the pressure sensor 94, the PLC switches the fluid pressure to the hydraulic cylinder 66 to reverse the direction of motion of the hydraulic cylinder 66 and raise up the sample collection probe 16 back to its uppermost position.

The feature of sensing and controlling the depth of penetration into the soil of the sample collection probe 16 is accomplished by providing a contact or proximity sensor 96 that is mounted to the sample receiving tube 16/76 above its bottom end for sensing the depth of the tube. The contact or proximity sensor 96 is electrically connected to the PLC 84. If a contact sensor is used to sense contact with the soil surface 20, the PLC is programmed to reverse the direction of the upper hydraulic actuator 66 and raise the sample receiving tube 16/76 with its soil sample when the contact sensor contacts the soil surface. However, it is preferred that a proximity sensor be used that detects the distance from the sensor to the soil surface 20 because a contact sensor tends to collect debris. With the proximity sensor, the sensed distance to the soil that is selected to cause the travel direction of the sample receiving tube 16/76 to be reversed and raise the sample receiving tube 16/76 is the distance from the proximity sensor to the bottom end of the sample receiving tube 16/76 less the desired depth of insertion of the sample receiving tube 16/76 into the soil for extracting a sample. The depth of insertion of the sample receiving tube 16/76 into the soil can be adjusted by reprogramming the PLC or alternatively the contact or proximity sensor can be releasably and slidably mounted to the sample receiving tube 16/76 for adjusting the vertical position of the sensor on the sample receiving tube 16/76.

The proximity sensor 96 signals to the PLC 84 that the mover 70 of the upper hydraulic actuator 66 has reached the preset desired lower limit of its motion. Another sensor, such as a limit switch or proximity or contact sensor, is desirably mounted to sense and signal to the PLC 84 that the mover 70 has reached a desired upper limit of its motion. Since such a limit sensor is well known in the prior art and is not a part of the invention, it is not illustrated.

The third enhancement feature is maintaining a downward force on the scraper as it moves across the soil surface 20. For this purpose a first flow control valve 98, having a first set point, is interposed in the fluid line 100 that is connected from the scraper cylinder down port of the manifold 86 to the down port 36D of the first actuator 36 that lowers the scraper. A second fluid line 102 is connected between the down port 36D and the hydraulic fluid return output 92 of the hydraulic circuit. The second fluid line 102 includes an interposed second flow control valve 104 having a second set point. The set points are selected to maintain a selected downward force on the scraper by maintaining a constant hydraulic pressure at the down port 36D of the first actuator. The set point for the flow control valve 98 principally controls the speed that the scraper moves downward and the set point for the flow control valve 104 principally controls the downward force that the scraper applies against the soil surface 20. Of course the actual set points for any particular hydraulic system are dependent upon the pump pressure of the hydraulic system and other hydraulic circuit components and system parameters so they are chosen by engineering design and subsequent testing. Other flow control valves may be used, as illustrated, for the purpose of controlling the speed of the motion of other actuators in the manner well known in the prior art.

As described above, the mobile support frame to which the soil sampling probe assembly 10 and the surface scraper assembly 12 are mounted is periodically stopped for taking a soil sample. While the sample collection probe 16 is raised in the position illustrated in FIG. 2, the scraper 34, 34A or 34C scrapes the debris from the soil surface 20 in the manner previously described. The scraper is then raised and retracted so the sample collection probe 16 will not collide with any part of the surface scraper assembly 12. The soil sampling probe assembly 10 extracts a soil sample in the manner described above and then returns the sample collection probe 16 to its raised position. In order to eject the soil sample from the sample collection probe 16 and drop it into a container, a container must be moved under the sample collection probe 16.

Figure 15:
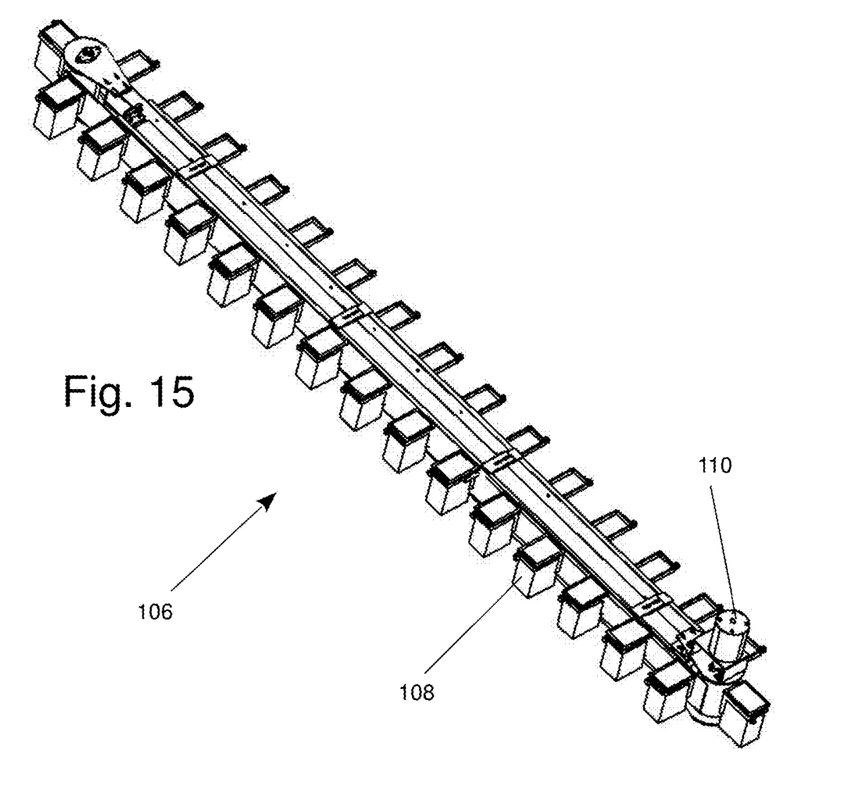
FIG. 15 is a view in perspective of a container conveyer that may be used with embodiments of the invention.

Although the containers could be positioned manually, preferably there is a container conveyer system that is also controlled by the PLC 84 which coordinates the operation of the conveyer system, the soil sampling probe assembly 10 and the surface scraper assembly 12. Because there are container conveyer systems known in the prior art that will work with embodiments of the invention, conveyer system details are not described. For example, the container conveyer system illustrated in patent application US 2013/0319763 could be adapted for use with the present invention by spacing its containers ("receiving stations") sufficiently far apart that the component parts of the soil sampling probe assembly 10 can pass between its containers. FIG. 15 illustrates a container conveyer 106 that has spaced apart containers 108 that are attached to a drive belt that is indexed around an elongated endless loop and driven by an electric motor 110. After each soil sample is retrieved and the sample collection probe 16 is raised, the conveyer moves a container under the sample receiving tube 76. The lower actuator 74 is then operated to slide the central rod downward and along the central passageway to eject the soil sample from the sample receiving tube 76 and the soil sample falls into the container. The conveyer is then moved so that the space between the containers provides sufficient clearance for operation of the soil sampling probe assembly 10

PARTS LIST WITH REFERENCE NUMBERS soil sampling probe assembly 10
surface scraper assembly 12
vertical support post 13
mobile support frame 14
sample collection probe 16
soil 18
soil surface 20
carriage 22
carriage track 24
carriage plate 26
cross beam 28
L-beam 30
scraper support arm 32
scraper 34
preferred scraper 34A
cutter scraper 34C
first actuator 36 of surface scraper assembly
second actuator 38 of surface scraper assembly
upstanding support bracket 40
tubular stabilizer brace 41
vertical blade 42 of scraper 34
top and bottom blade flanges 44
bottom plate 46 of scraper 34
base plate 48 of scraper 34A
downward protruding ridge 50 of scraper 34A
upturned end 52 of scraper 34A
ribs 54 of scraper 34A cutter blade 56
vanes 58 on cutter blade 56
motor cover disk 60
vanes 62 on motor cover disk 60
box 64 of cutter scraper 34C
upper hydraulic actuator 66
stator 68 of upper hydraulic actuator 66
mover 70 upper hydraulic actuator 66
stator 72 of lower hydraulic actuator 74
lower hydraulic actuator 74
sample receiving tube 76
guide bar 78
vertical guide channels 80
support arms 82
PLC 84
multi-conductor cable 85
hydraulic manifold 86
manifold outlet ports 88
pressure in port 90
fluid return port 92
barrier pressure sensor 94
contact or proximity sensor 96
first flow control valve 98
fluid line 100
fluid line 102
flow control valve 104
container conveyer 106
containers 108
conveyer electric motor 110

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. A soil sample collection machine having a mobile support frame that is transportable across the soil surface of an agricultural field and further comprises:
   (a) a soil sampling probe assembly that is mounted to the mobile support frame and includes a sample collection probe and a first driver that is adapted to move the sample collection probe along a downward path into the soil to collect a sample of soil at the end of the downward path, to retract the probe upward and to eject the soil sample from the probe; and
   (b) a surface scraper assembly that is movably mounted to the mobile support frame and includes a scraper and a second driver that is adapted to lower the scraper onto the surface of the soil and move the scraper across an intersection of said downward path with the soil surface for removing surface debris before the sample collection probe is driven into the soil and removes the soil sample
   wherein the surface scraper assembly comprises
   (b1) a carriage that is slidable along a track that is attached to the mobile support frame;
   (b2) a scraper support arm that is pivotally mounted near a first end to the carriage;
   (b3) wherein the scraper is mounted near an opposite second end of the support arm for removing debris from the soil surface; and wherein
   (b4) the second driver comprises
      (i) a first actuator attached between the carriage and the scraper support arm and adapted to lower the scraper onto the soil surface and to raise the scraper from the soil surface; and
      (ii) a second actuator attached between the mobile support frame and the carriage and adapted to slide the carriage along the track and thereby move the scraper along the soil surface and across the downward path beneath the sample collection probe.

2. A soil sample collection machine in accordance with claim 1 wherein the first actuator is a hydraulic actuator that is connected in a hydraulic circuit that includes a first fluid line connected from a pressure input of the hydraulic circuit to a down port of the first actuator for lowering the scraper, wherein the first fluid line includes an interposed first flow control valve having a first set point and wherein a second fluid line is connected between said down port and a fluid return output of the hydraulic circuit and the second fluid line includes an interposed second flow control valve having a second set point, the first set point and the second set point selected to maintain a selected downward force on the scraper by maintaining a constant hydraulic pressure at the down port of the first actuator.

3. A soil sample collection machine in accordance with claim 1 wherein the scraper is a push blade scraper.

4. A soil sample collection machine in accordance with claim 1 wherein the scraper is a drag scraper having a base plate with a downward protruding ridge on the underside of the base plate that is oriented transverse of the scraper support arm and positioned distally from the support arm.

5. A soil sample collection machine in accordance with claim 1 wherein the scraper is a cutter scraper comprising a cutter blade driven in rotation and adapted to cut through debris on the soil surface and push the cut debris from beneath the soil sampling probe.

6. A soil sample collection machine in accordance with claim 5 wherein the cutter scraper further comprises a plurality of outward extending vanes or arms that are driven in rotation with the cutter blade for throwing cut debris outward away from the cutter blade.

7. A soil sample collection machine in accordance with claim 1 wherein the soil sampling probe assembly further comprises:
   (a) said first driver comprising
      (i) an upper actuator having a first stator fixed to the mobile support frame and a first mover extending downward; and
      (ii) a lower actuator having a second stator attached to the mover of the upper actuator and a second mover extending downward;
   (b) a sample receiving tube that forms the sample collection probe and has a central passageway the sample receiving tube being fixed to the second stator; and
   (c) a rod slidable along the central passageway of the sample receiving tube and attached to the second mover;
   wherein the upper actuator is adapted to lower the lower actuator and with it lower the tube through the soil surface into soil and collect the soil sample within the central passageway and then raise the lower actuator and with it the tube and wherein the lower actuator is adapted to slide the rod along the central passageway and eject the soil sample from the tube.

8. A soil sample collection machine in accordance with claim 7 wherein the upper actuator is a hydraulic actuator that is connected in a hydraulic circuit that includes a fluid line connected to a port of the hydraulic actuator for lowering the lower actuator and with it the tube, the fluid line also including a pressure sensor having a set point for detecting a collision of the tube with a rock, the hydraulic circuit adapted to reverse the hydraulic actuator and raise the lower actuator and with it the tube when the pressure sensor senses the set point.

9. A soil sample collection machine in accordance with claim 7 wherein a contact or proximity sensor is mounted to the sample receiving tube above its bottom end for sensing the depth of the tube.

10. A soil sample collection machine in accordance with claim 9 wherein the contact or proximity sensor is releasably and slidably mounted to the sample receiving tube for adjusting the depth of probe penetration.

\* \* \* \* \*